United States Patent [19]

Eloranta

[11] Patent Number: 4,960,939

[45] Date of Patent: Oct. 2, 1990

[54] PROCESS FOR THE PREPARATION OF 3,4-DI-METHOXY-N-METHYL-PHENE-THYLAMINE

[75] Inventor: Maire M. Eloranta, Oulu, Finland

[73] Assignee: Farmos-Yhtyma Oy, Turku, Finland

[21] Appl. No.: 620,288

[22] Filed: Jun. 13, 1984

[30] Foreign Application Priority Data

Jun. 14, 1983 [FI] Finland ................................. 832128

[51] Int. Cl.$^5$ .............................................. C07C 87/28
[52] U.S. Cl. ..................................... 564/374; 564/375
[58] Field of Search ......................... 564/142, 374, 372

[56] References Cited

U.S. PATENT DOCUMENTS

| | | | |
|---|---|---|---|
| 2,006,114 | 6/1935 | Rosenmund et al. | 564/374 |
| 2,400,038 | 5/1946 | Buck et al. | 560/142 X |
| 2,798,094 | 7/1957 | Shepard et al. | 564/374 |
| 4,152,353 | 5/1979 | Habermann | 564/374 |
| 4,181,738 | 1/1980 | Ginos et al. | 564/374 X |
| 4,190,601 | 2/1980 | Decker et al. | 564/374 |
| 4,340,603 | 7/1982 | Bodor et al. | 564/374 X |

OTHER PUBLICATIONS

Skita et al Berichte der Deutschen Chemischen Gesellschaft 61 pp. 1682-1692 (1928).
Moller et al Houben-Weyl, XI/1, pp. 644-652.
Shirahata et al Chem. Pharm. Bull. 30 (4) pp. 1352-1357 (1982).
Ruchirawat et al, Synthetic Communication 14 (13) pp. 1221-1228 (1984).
Buck et al. (II), "Jour. Amer. Chem. Soc.," vol. 64, pp. 2263-2264 (1942).
Adams et al., "Organic Reactions", vol. V., p. 325 (1952).

*Primary Examiner*—Robert V. Hines
*Attorney, Agent, or Firm*—Armstrong, Nikaido, Marmelstein, Kubovcik & Murray

[57] ABSTRACT

N-benzyl-N-methyl-3,4-dimethoxyphenethylamine is prepared by reacting 3,4-dimethoxyphenethylamine with a mixture of benzaldehyde and formaldehyde in the presence of hydrogen and a catalyst such as palladium on carbon.

2 Claims, No Drawings

PROCESS FOR THE PREPARATION OF 3,4-DI-METHOXY-N-METHYL-PHENETHYLAMINE

The present invention provides a new process for the preparation of 3,4-di-isobutyryloxy-N-methylphenethylamine (I) or ibopamine.

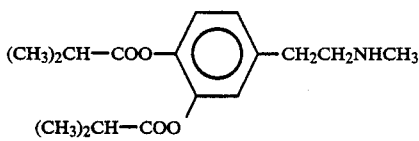

and the pharmaceutically acceptable acid addition salts of ibopamine and a certain novel N-benzyl-N-methyl phenethylamine useful in the process.

Ibopamine is a well-known cardiac medicine, which is used especially in heart and kidney insufficiency.

Only two processes for the preparation of ibopamine are known. These are described in e.g. the GB-patent No. 1551661. The processes can be represented by the following formula schemes:

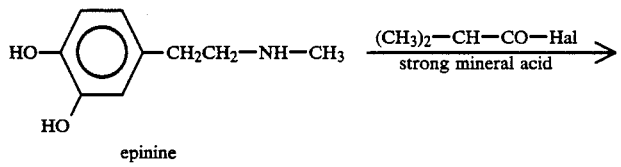

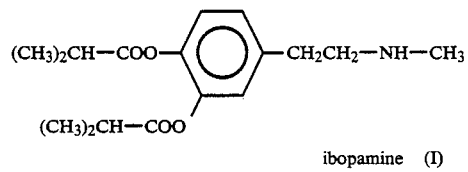

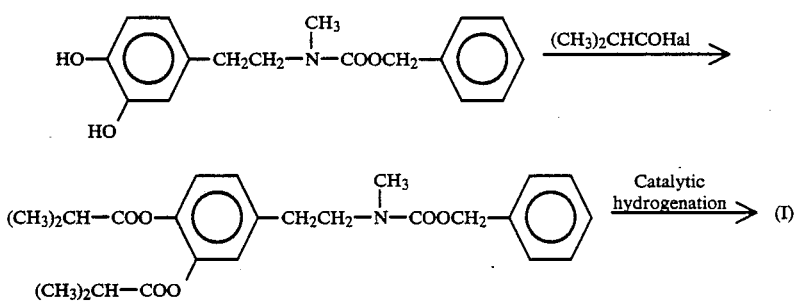

Hal = halogen

The process thus has either 1 or 3 steps, but in both cases is started from epinine, which is an expensive agent and difficult to obtain. In the patent no yields are mentioned. Since no protective group is used in the one-stage process the yield presumably is low, because side products probably are formed in the reaction. In addition to this the esterification is performed with only acid chloride without base. Usually esterification of phenol groups without base is a slow and incomplete reaction. In the 3-stage process the corresponding acetamide is probably formed in the last hydrogenation step, for which reason this process too cannot give very good yields.

The process of the present invention is started from a different starting material, namely 3,4-dimethoxyphenethylamine, which is a cheap large-scale raw material. The process for producing ibopamine has 4 steps, but since the starting material is much less expensive than epinine and all steps succeed with excellent yields and are easy to perform also on a technical scale, the process is considerably more advantageous than the above described known processes.

According to the present invention ibopamine and its pharmaceutically acceptable salts are produced by a process which comprises
(a) reaction of 3,4-dimethoxyphenethylamine with benzaldehyde and formaldehyde in the presence of hydrogen and a catalyst to give a compound of formula (II)

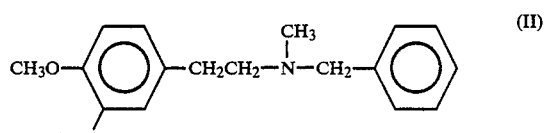

(b) conversion of the methoxy groups of a compound of formula II into hydroxyl groups to give a compound of formula III

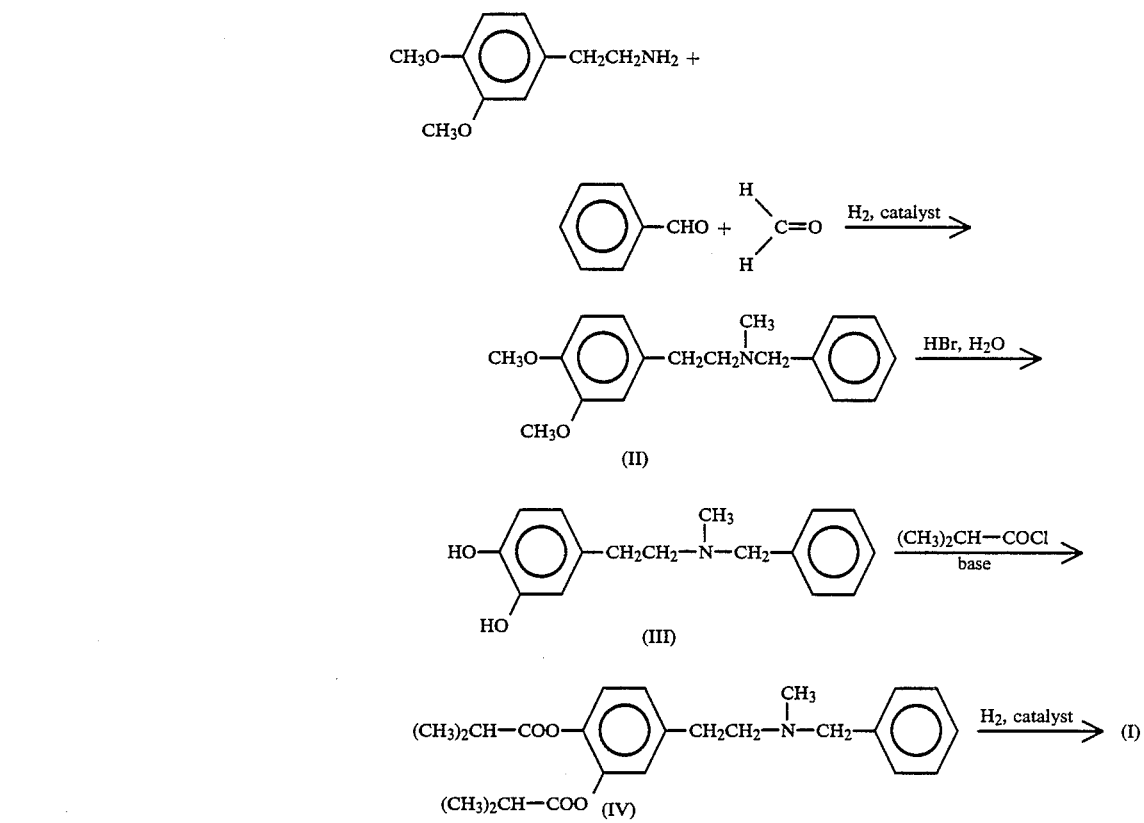

(c) reaction of a compound of formula III with isobutyryl chloride in the presence of a base to give a compound of formula IV

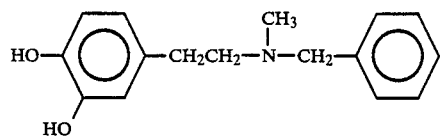

(d) catalytic hydrogenation to give a compound of formula (I).

A compound of the formula IV, which may be represented by

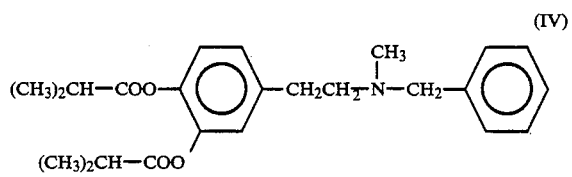

in which R is isobutyryloxy, and salts thereof is a novel intermediate and as such is within the scope of the present invention.

The new process for producing ibopamine can be represented by the following reaction scheme:

The first step of this process is especially inventive. In the first place as mentioned the process is started from a cheap starting material. Secondly the monomethylation of a primary amine in good yield is often difficult as can be seen from e.g. the publication S. Krishnamurthy, Tetrahedron Letters 23 (1982) 3315. In the process of the invention the methyl group and the benzyl protecting group are simultaneously attached to the amino group of the starting material. Although similar processes can be found in the literature, the reaction has not been adapted in the same way as in the process of the invention.

In the publication K. Fujimori et al., Tetrahedron Letters 21 (1980) 3358-8 the reductive alkylation of amines with e.g. benzaldehyde and formalin in an excess of selenophenol is described. In the publication D. B. Repke et al., Tetrahedron Letters 20 (1979) 4183-4 is described the reaction of N-methyl-benzylamine with a carbonyl compound which is followed by catalytic hydrogenation.

In the present invention this simultaneous monomethylation and benzyl protection is inventive. The benzyl group is, when considering the whole synthesis series, a very good protecting group because it is stable in both acid and basic conditions. The benzyloxycarbonyl protecting group could not have been used because it is split off under acid conditions (McOmie: Protective Groups in Organic Chemistry, Plenum Press, London and New York 1973, 56).

In the following step the methoxy groups are converted by a known procedure to hydroxyl groups. The yield is excellent. When the obtained intermediate (III), which does not have to be isolated, in the next step is esterified with isobutyryl chloride in the presence of a base, this step too succeeds with good yield. In the last step the benzyl protecting group is removed by hydrogenation in the presence of a catalyst, which also is an almost quantitatively succeeding reaction.

Because the isolation of the intermediate (III) is not necessary the process of the invention is in practice a 3-step process.

In the first step 3,4-dimethoxyphenethylamine, benzaldehyde and formaldehyde are hydrogenated in the presence of a catalyst, e.g. palladium on carbon, either at normal or slightly elevated pressure, preferably a pressure of 2-3 atm (0.2-0.3 MPa), and the temperature is room temperature or slightly elevated temperature, preferably 20°-30° C. As solvent is used an organic solvent, e.g. ethanol or an ethanol-methylenechloride (1:1)-mixture. The desired product, N-benzyl-N-methyl-3,4-dimethoxyphenethylamine (II) is obtained in a very pure state, when it is precipitated as an acid addition salt, e.g. hydrobromide. As free base the product is oily and difficult to handle.

In the second step the methoxy groups are converted to hydroxyl groups e.g. by boiling in concentrated hydrobromic acid in a nitrogen atmosphere. After neutralization the product II is extracted into an organic solvent, for instance methylene chloride, to which is added isobutyryl chloride as such or dissolved in an organic solvent. The esterification is performed in the presence of a base at a low temperature, preferably below 30° C. As base is used e.g. an organic base such as an organic amine, preferably triethylamine. The compound (IV) is isolated as an acid addition salt, e.g. by passing hydrogen chloride gas into the solution which gives the IV hydrochloride. It is advantageous to isolate the product in the form of a salt and use this in the next hydrogenation step. If the compound (IV) is used as base in the hydrogenation there is formed as by-product the corresponding acetamide.

In the last step the benzyl protecting group is removed by hydrogenation in the presence of a catalyst, for instance palladium on carbon. The pressure is normal or slightly elevated pressure, preferably 2-3 atm (0.2-0.3 MPa). The temperature is room temperature or elevated temperature, e.g. 20°-50° C. As solvent is used an organic solvent, preferably glacial acetic acid. If the starting material is IV×HCl the end product is obtained as hydrochloride. When desired the base can be liberated and converted to other salts by common methods.

The invention is described in more detail in the following examples.

The NMR spectra have been determined with a Bruker WP 80 DS apparatus. The shifts are presented as ppm from TMS. The mass-spectra have been determined with a Kratos MS80RF apparatus either by electron impact (EI) or chemical ionisation (CI) using direct inlet.

EXAMPLE 1

N-benzyl-N-methyl-3,4-dimethoxyphenethylamine hydrobromide (II×HBr)

45,3 g (0,25 mol) 3,4-dimethoxyphenethylamine, 26,5 g (0,25 mol) benzaldehyde and 32,5 ml 35 % formalin solution is hydrogenated in the presence of 1,2 g 10 % Pd/C catalyst at a pressure of 2-3 atm. at 20°-30° C. in 35 ml ethanol. The catalyst is filtered off and the product II is precipitated as hydrobromide by adding 29 ml 48 % hydrobromic acid. The yield is 83,3 g (91,0 %) and the m.p. is 213°-215° C. (from ethanol).

COMPOUND II $^1$H-NMR (CDCl$_3$): 2.26 ppm (3H, s), 2.37-2.95 ppm (4H, m), 3.53 (2H, s), 3.81 (6H, s), 6.70 {3H, s), 7.26 (5H, s).

$^{13}$C-NMR (CDCl$_3$): 33.6 (t), 42.2 (q), 55.9 (q), 56.0 (q), 59.3 (t), 62.2 (t), 111.6 (d), 112.4 (d), 120.6 (d), 126.8 (d), 128.1 (d), 128.9 (d), 133.3 (s), 139.1 (s), 147.5 (s), 148.9 (s).

MS[CI(NH$_3$)]: m/z 286 (M+1).

EXAMPLE 2

N-Benzyl-N-methyl-3,4-di-isobutyryloxyphenethylamine hydrochloride (IV×HCl)

73,3 g (0,20 mol) of compound II×HBr prepared according to example 1 and 150 ml 48 % hydrobromic acid are boiled in nitrogen atmosphere for 2 hours. The pH of the cooled solution is adjusted to 8-9 and the formed N-benzyl-N-methyl-3,4-dihydroxyphenethylamine (III) is extracted into methylene chloride.

[If one wishes to isolate the intermediate III, the methylene chloride solution is evaporated to dryness and the product crystallized from ethyl acetate, m.p. 113°-115° C.]. To the dried methylene chloride solution is added 57,0 ml (0,41 mol) triethylamine and to the mixture is dropwise slowly added 42,9 ml (0,41 mol) isobutyryl chloride dissolved in methylene chloride while the temperature of the reaction mixture is kept below 30° C. When the reaction is completed water is added to the mixture and the layers are separated. Into the dried methylene chloride layer is passed dry HCl-gas 4,5 l, after which the solvent is evaporated and the product (IV×HCl) is crystallized from ethyl acetate. The yield is 78,1 g (90,0 %). M.p. 154,5°-157,5° C.

COMPOUND III:

$^1$H-NMR (CD$_3$OD): 2.26 (3H, s), 2.42-2.80 (4H, m), 3.56 (2H, s), 6.37-6.75 (3H, m), 7.30 {5H, s).

$^{13}$C-NMR (CDCl$_3$+CD$_3$OD): 32.8 (t), 41.8 (q), 59.1 (t), 61.9 (t), 115.0 (d), 115.5 (d), 120.2 (d), 127.2 (d), 128.2 (d), 129.4 (d), 132.1 (s), 137.6 (s), 142.7 (s), 144.3 (s).

MS[CI (NH$_3$)]: m/z 258 (M+1).

COMPOUND IV:

$^1$H-NMR (CDCl$_3$): 1.29 (12H, d), 2.25 (3H, s), 2.42-3.10 (6H, m), 3,54 (2H, s), 6.87 (1H, br. s), 7.02 (2H, br. s), 7.35 (5H, s).

$^{13}$C-NMR (CDCl$_3$): 18.9 (q), 33.3 (t), 34.0 (d), 42.1 (q), 58.7 (t), 62.2 (t), 122.9 (d), 123.5 (d), 126.5 (d), 126.9 (d), 128.2 (d), 128.9 (d), 138.9 (s), 139.1 (s), 140.3 (s), 142.1 (s), 174.3 (s).

MS(EI, 70eV): m/z 397 (5), 134 (100), 91 (95).

EXAMPLE 3

3,4-di-isobutyryloxy-N-methyl-phenethylamin hydrochloride (I×HCl), ibopamine hydrochloride 60,0 g of the product according to example 2 (IV×HCl) is hydrogenated in acetic acid in the presence of 1,25 g 10% Pd/C catalyst at a pressure of 2-3 atm (0.2-0.3 MPa). The temperature being 20°-50° C. When the reaction is completed the solvent is evaporated and the formed ibopamine hydrochloride (I×HCl) is crystallized from ethyl acetate. The yield is 45,4 g (95,5%). M.p. 131°-6° C.

COMPOUND I×HCl:

$^{13}$C-NMR (CDCl$_3$): 18.9 (q), 31.6 (t), 33.1 (q), 34.0 (d), 50.3 (t), 123.8 (d), 126.7 (d), 134.9 (s), 141.4 (s), 142.5 (s), 174.2 (s).

MS[CI (NH$_3$)]: m/z 308 (M+1).

I claim:

1. A process for producing a compound of formula II

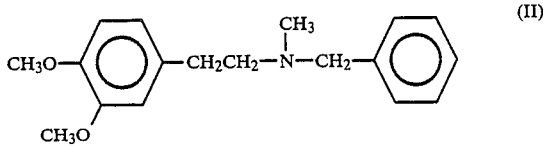

which comprises reacting 3,4-dimethoxyphenethylamine with a mixture of benzaldehyde and formaldehyde in the presence of hydrogen and a catalyst to give a compound of formula (II).

2. A process according to claim 1 wherein the catalyst is palladium on carbon.

* * * * *